US012178655B2

(12) United States Patent
Luo et al.

(10) Patent No.: US 12,178,655 B2
(45) Date of Patent: *Dec. 31, 2024

(54) METHOD FOR GENERATING CONTRAST ENHANCED ULTRASOUND IMAGES WITH VARIED IMAGING PARAMETERS AND ULTRASOUND IMAGING DEVICE PERFORMING THE METHOD

(71) Applicants: BEIJING SHEN MINDRAY MEDICAL ELECTRONICS TECHNOLOGY ACADEMY CO., LTD., Beijing (CN); GENERAL HOSPITAL OF CHINESE PLA, Beijing (CN); SHENZHEN MINDRAY BIO-MEDICAL ELECTRONICS CO., LTD., Guangdong (CN)

(72) Inventors: Yukun Luo, Beijing (CN); Xiang Fei, Beijing (CN); Xirui Zhang, Beijing (CN); Maodong Sang, Beijing (CN); Lei Zhu, Beijing (CN); Yuxin Chen, Shenzhen (CN); Yan Zhang, Beijing (CN); Fang Xie, Beijing (CN); Yiru Wang, Beijing (CN); Duo Dong, Shenzhen (CN)

(73) Assignees: Beijing Shen Mindray Medical Electronics Technology Academy Co., Ltd., Beijing (CN); General Hospital of Chinese PLA, Beijing (CN); Shenzhen Mindray Bio-Medical Electronics Co., Ltd., Shenzhen (CN)

(*) Notice: Subject to any disclaimer, the term of this patent is extended or adjusted under 35 U.S.C. 154(b) by 0 days.

This patent is subject to a terminal disclaimer.

(21) Appl. No.: 18/132,086

(22) Filed: Apr. 7, 2023

(65) Prior Publication Data

US 2023/0240660 A1 Aug. 3, 2023

Related U.S. Application Data

(63) Continuation of application No. 16/883,884, filed on May 26, 2020, now Pat. No. 11,672,512, which is a (Continued)

(51) Int. Cl.
*A61B 8/08* (2006.01)
*A61B 8/00* (2006.01)
*A61B 8/06* (2006.01)

(52) U.S. Cl.
CPC .............. *A61B 8/5207* (2013.01); *A61B 8/06* (2013.01); *A61B 8/461* (2013.01); *A61B 8/481* (2013.01)

(58) Field of Classification Search
None
See application file for complete search history.

(56) References Cited

U.S. PATENT DOCUMENTS 5,469,849 A 11/1995 Sasaki et al.
5,588,434 A 12/1996 Fujimoto
(Continued)

FOREIGN PATENT DOCUMENTS

CN 101854537 A 10/2010
CN 102123668 A 7/2011
(Continued)

OTHER PUBLICATIONS

PCT International Search Report and the Written Opinion mailed Aug. 17, 2018, issued in related International Application No. PCT/CN2017/113307 with partial English translation (9 pages).
(Continued)

*Primary Examiner* — Joel Lamprecht
*Assistant Examiner* — Nyrobi Celestine

(74) *Attorney, Agent, or Firm* — Sheppard Mullin Richter & Hampton LLP

(57) ABSTRACT

Embodiments of the present disclosure provide a contrast enhanced ultrasound imaging method and an ultrasound imaging device. The method may include: determining a target imaging mode from preset imaging modes in response to the first instruction, where the preset imaging modes comprise a first contrast enhanced imaging mode and a second contrast enhanced imaging mode which have different frame rate; transmitting ultrasound waves to a target object and receiving ultrasound echoes returned from the target object according to the determined target imaging mode to obtain ultrasound echo signals; and generating a contrast enhanced image according to the ultrasound echo signals. An ultrasound imaging device is also be provided.

13 Claims, 8 Drawing Sheets

Related U.S. Application Data continuation of application No. PCT/CN2017/113307, filed on Nov. 28, 2017.

(56) References Cited

U.S. PATENT DOCUMENTS

| | | | |
|---|---|---|---|
| 5,873,829 | A | 2/1999 | Kamiyama et al. |
| 7,993,273 | B2 | 8/2011 | Phillips et al. |
| 9,788,815 | B2 | 10/2017 | Wan et al. |
| 2003/0097070 | A1 | 5/2003 | Nakaya et al. |
| 2009/0054775 | A1* | 2/2009 | Kato ............... G01S 7/52046 600/443 |
| 2009/0171207 | A1* | 7/2009 | Imamura ............... A61B 8/08 600/443 |
| 2009/0312642 | A1 | 12/2009 | Satoh |
| 2009/0326379 | A1 | 12/2009 | Daigle et al. |
| 2011/0026676 | A1 | 2/2011 | Takekoshi |
| 2012/0203112 | A1 | 8/2012 | Lazebnik |
| 2015/0087985 | A1 | 3/2015 | Yoshiara et al. |
| 2015/0146852 | A1 | 5/2015 | Sung et al. |
| 2015/0209006 | A1 | 7/2015 | Kawagishi et al. |
| 2015/0257701 | A1 | 9/2015 | Horinaka et al. |
| 2015/0363104 | A1* | 12/2015 | Ichioka ............... A61B 8/465 345/173 |
| 2015/0374337 | A1* | 12/2015 | Nishihara ............... A61B 8/464 600/443 |
| 2016/0331350 | A1 | 11/2016 | Duncan et al. |
| 2017/0231599 | A1* | 8/2017 | Jago ............... A61B 8/5207 600/438 |
| 2018/0003811 | A1 | 1/2018 | Pellegretti et al. |
| 2018/0035979 | A1 | 2/2018 | Herbst et al. |
| 2018/0214134 | A1 | 8/2018 | Kim et al. |

FOREIGN PATENT DOCUMENTS

| | | |
|---|---|---|
| CN | 103156636 A | 6/2013 |
| CN | 103860201 A | 6/2014 |
| CN | 104665855 A | 6/2015 |
| WO | 99-59473 A1 | 11/1999 |

OTHER PUBLICATIONS

PCT International Preliminary Report on Patentability mailed Jun. 11, 2020, issued in related International Application No. PCT/CN2017/113307 with partial English translation (10 pages).
Non-Final Office Action dated Oct. 14, 2021, issued in related U.S. Appl. No. 16/883,884 (42 pages).
Final Office Action dated Mar. 24, 2022, issued in related U.S. Appl. No. 16/883,884 (37 pages).
Non-Final Office Action dated Sep. 8, 2022, issued in related U.S. Appl. No. 16/883,884 (10 pages).
Notice of Allowance mailed Feb. 1, 2023, issued in related U.S. Appl. No. 16/883,884 (9 pages).

* cited by examiner

METHOD FOR GENERATING CONTRAST ENHANCED ULTRASOUND IMAGES WITH VARIED IMAGING PARAMETERS AND ULTRASOUND IMAGING DEVICE PERFORMING THE METHOD

CROSS REFERENCE TO RELATED APPLICATIONS

The present application is a continuation of U.S. application Ser. No. 16/883,884, filed on May 26, 2020, and entitled "Method for Generating Contrast Enhanced Ultrasound Images with Varied Imaging Parameters and Ultrasound Imaging Device Performing the Method", which is a continuation of International Application No. PCT/CN2017/113307, filed with the China National Intellectual Property Administration on Nov. 28, 2017, and entitled "Radiographic Imaging Method and Ultrasonic Imaging Device". The contents of the above-identified applications are incorporated herein by reference in their entirety.

TECHNICAL FIELD

The present disclosure relates to ultrasound imaging, particularly to a contrast enhanced imaging method and an ultrasound imaging device

BACKGROUND

In recent years, contrast enhanced ultrasound imaging has played an increasingly important role in the diagnosis of malignant diseases such as liver cancer, thyroid cancer and breast cancer, etc. In particular, abdominal contrast enhanced imaging, represented by liver contrast enhanced imaging, has formed a unified clinical standard. For contrast enhanced ultrasound examination on organs such as thyroid, carotid artery and breast, etc., Europe and China have also issued corresponding clinical application guidelines.

Currently, the ultrasound imaging device can obtain dynamic high-contrast enhanced images presenting the blood perfusion of the lesion and the surrounding normal tissues. Compared with normal tissues, the micro blood flow of malignant lesion tissues is more abundant and the metabolic level is higher. The typical performance of the hemodynamics of the malignant lesion is rapid enhancement and rapid regression. In order to present the hemodynamic differences between the normal tissues and the malignant lesions, the contrast enhanced imaging is required to have a certain frame rate. At the same time, in order to reduce the damage to the microbubbles so as to maximize the duration of the contrast, the common ultrasound imaging device usually has a frame rate of 10 frame per second (fps) to 15 fps, and the frame rate cannot be changed during the imaging.

Therefore, the existing ultrasound imaging device has fixed frame rate (such as 10 fps to 15 fps). When diagnosing certain diseases (such as small blood-rich lesions), it may be difficult to obtain accurate or satisfactory contrast enhanced images with the fixed frame rate, which increases the difficulty of diagnosing the disease to a certain extent.

SUMMARY

The embodiments of the present disclosure provide contrast enhanced imaging methods and ultrasound imaging devices in which an imaging mode can be selected according to requirements, and the contrast enhanced images can be generated according to the imaging mode. Therefore, it is not required to adjust the frame rate of the ultrasound imaging device multiple times, and the flexibility of the contrast enhanced imaging is increased.

In one embodiment of the present disclosure, a contrast enhanced imaging method is provided, which may include:
receiving a first instruction;
determining a target imaging mode from preset imaging modes in response to the first instruction, wherein, the preset imaging modes comprise a first contrast enhanced imaging mode and a second contrast enhanced imaging mode, and a frame rate of the first contrast enhanced imaging mode is different from a frame rate of the second contrast enhanced imaging mode;
transmitting ultrasound waves to a target object and receiving ultrasound echoes returned from the target object according to the determined target imaging mode to obtain ultrasound echo signals; and
generating a contrast enhanced image according to the ultrasound echo signals.

In one embodiment of the present disclosure, a contrast enhanced imaging method is provided, which may include:
transmitting ultrasound waves to a target object and receiving ultrasound echoes returned from the target object according to a first contrast enhanced imaging mode to obtain a first ultrasound echo signal;
generating a first contrast enhanced image according to the first ultrasound echo signal;
receiving a mode switching instruction to switch to a second contrast enhanced imaging mode, wherein a frame rate of the first contrast enhanced imaging mode is different from a frame rate of the second contrast enhanced imaging mode;
transmitting ultrasound waves to the target object and receiving ultrasound echoes returned from the target object according to the second contrast enhanced imaging mode to obtain a second ultrasound echo signal; and
generating a second contrast enhanced image according to the second ultrasound echo signal.

In one embodiment of the present disclosure, an ultrasound imaging device is provided, which may include:
a probe;
a transmitting circuit which excites the probe to transmit ultrasound waves to a target object;
a receiving circuit which receives ultrasound echoes returned from the target object through the probe to obtain an ultrasound echo signal;
a processor configured to process the ultrasound echo signal to obtain an ultrasound image of the target object;
a display which displays the ultrasound image;
wherein the processor is further configured to:
receive a first instruction;
determine a target imaging mode from preset imaging modes in response to the first instruction, wherein, the preset imaging modes comprise a first contrast enhanced imaging mode and a second contrast enhanced imaging mode, and a frame rate of the first contrast enhanced imaging mode is different from a frame rate of the second contrast enhanced imaging mode;
transmit ultrasound waves to the target object and receive ultrasound echoes returned from the target object according to the determined target imaging mode to obtain ultrasound echo signals; and generate a contrast enhanced image according to the ultrasound echo signals.

In one embodiment of the present disclosure, an ultrasound imaging device is provided, which may include:

a probe;

a transmitting circuit which excites the probe to transmit ultrasound waves to a target object;

a receiving circuit which receives ultrasound echoes returned from the target object through the probe to obtain an ultrasound echo signal;

a processor configured to process the ultrasound echo signal to obtain an ultrasound image of the target object;

a display which displays the ultrasound image;

wherein the processor is further configured to:

transmit ultrasound waves to a target object and receive ultrasound echoes returned from the target object according to a first contrast enhanced imaging mode to obtain a first ultrasound echo signal;

generate a first contrast enhanced image according to the first ultrasound echo signal;

receive a mode switching instruction to switch to a second contrast enhanced imaging mode, wherein a frame rate of the first contrast enhanced imaging mode is different from a frame rate of the second contrast enhanced imaging mode;

transmit ultrasound waves to the target object and receive ultrasound echoes returned from the target object according to the second contrast enhanced imaging mode to obtain a second ultrasound echo signal; and generate a second contrast enhanced image according to the second ultrasound echo signal.

In one embodiment of the present disclosure, a computer-readable storage medium may be provided on which instructions may be stored. The instructions, when be executed in a computer, may enable the computer to execute the methods above.

In the technical solutions provided by the embodiments of the present disclosure, the ultrasound imaging device may transmit ultrasound waves to the target object and receive the ultrasound echoes returned from the target object to obtain the echo signals to generate the contrast enhanced image according to the imaging mode selected by the user. This way, the imaging mode can be selected according to the diagnosis needs, and the contrast enhanced image can be generated according to the imaging mode. Therefore, the contrast enhanced imaging is more flexible and more accurate or satisfactory contrast enhanced image can be obtained, thereby reducing the difficulty of the diagnosis to the disease.

BRIEF DESCRIPTION OF THE DRAWINGS

FIG. 4 (b) is a schematic diagram of an interface for selecting the second contrast enhanced imaging mode in one embodiment of the present disclosure;

DETAILED DESCRIPTION

The technical solutions in the embodiments of the present disclosure will be described clearly and completely in connection with the drawings. Obviously, the described embodiments are only a part, but not all of the embodiments of the present disclosure.

The terms "first", "second", "third", "fourth", etc. (if any) in the description, claims and the drawings of the present disclosure are used to distinguish similar objects, but not mean a specific order or sequence. It should be understood that the data used in this way can be interchanged in appropriate circumstances so that the embodiments described herein can be implemented in an order other than what is illustrated or described herein. In addition, the terms "including" and "having" and any variations thereof are intended to mean non-exclusive inclusions. For example, the processes, methods, systems, products or devices that contain a series of steps or units will not be limited to those clearly listed steps or units, but may include other steps or units not explicitly listed or inherent to these processes, methods, products, or devices.

Figure 1:
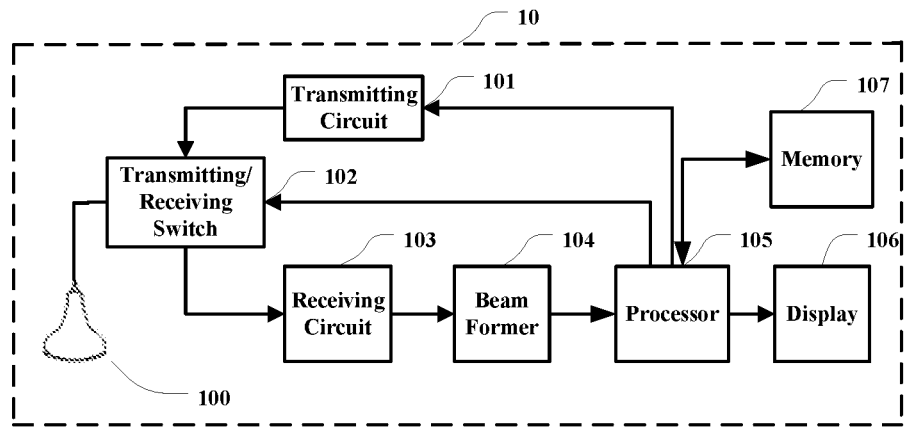
FIG. 1 is a schematic block diagram of an ultrasound imaging device in one embodiment of the present disclosure.

FIG. 1 is a schematic block diagram of an ultrasound imaging device 10 in one embodiment of the present disclosure. The ultrasound imaging device 10 may include a probe 100, a transmitting circuit 101, a transmitting/receiving switch 102, a receiving circuit 103, a beam former 104, a processor 105 and a display 106. The transmitting circuit 101 may excite the probe 100 to transmit ultrasound waves to a target object. The receiving circuit 103 may receive the ultrasound echoes returned from the target object through the probe 100, thereby obtaining ultrasound echo signals. After the beam forming process is performed thereon by the beam former 104, the ultrasound echo signals may be sent to the processor 105. The processor 105 may process the ultrasound echo signals to obtain the ultrasound image of the target object. The ultrasound image obtained by the processor 105 may be stored in a memory 107. These ultrasound images may be displayed on the display 106.

In the embodiments of the present disclosure, the display 106 of the ultrasound imaging device 10 may be a touch or a liquid crystal display screen, etc. Alternatively, the display 106 may be an independent display device such as a liquid crystal display or a television independent of the ultrasound imaging device 10, or the display screen on an electronic devices such as a mobile phone or a tablet computers, etc.

In the embodiments of the present disclosure, the memory 107 of the ultrasound imaging devices 10 may be a flash memory, a solid-state memory, a hard disk, or the like.

In one embodiment of the present disclosure, a computer-readable storage medium may also be provided. The computer-readable storage medium may store multiple program instructions which, after being called and executed by the processor 105, may implement a part or all or any combination of the steps in the contrast enhanced imaging methods in the embodiments above.

In some embodiments, the computer-readable storage medium may be the memory 107, which may be a non-volatile storage medium such as a flash memory, a solid state memory, a hard disk or the like.

In the embodiments of the present disclosure, the processor 105 of the ultrasound imaging devices 10 may be implemented by software, hardware, firmware or a combination thereof, or may use a circuit, one or more application specific integrated circuits (ASIC), one or more general-purpose integrated circuits, one or more microprocessors, one or more programmable logic devices, or combinations of the circuits or devices above, or other suitable circuits or devices, such that the processor 105 can execute the steps of the contrast enhanced imaging methods in the embodiments above.

Figure 2:
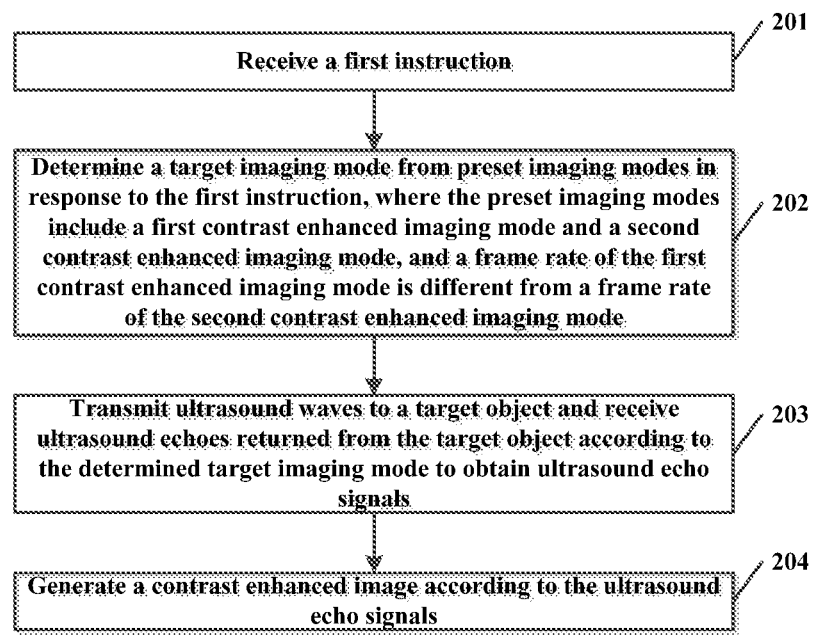
FIG. 2 is a schematic flowchart of a contrast enhanced imaging method in one embodiment of the present disclosure.

The contrast enhanced imaging methods of the present disclosure will described in detail below. Referring to FIG. 2, a contrast enhanced imaging method may be provided in one embodiment of the present disclosure, which may be applied to the ultrasound imaging device 10, and particularly suitable for the ultrasound imaging device 10 including a touch screen in which the touch operations may be used to input instructions. The ultrasound imaging device 10 may be used to generate a contrast enhanced image. The contrast enhanced imaging method may include the following steps.

In step 201, a first instruction may be received.

In one embodiment, the processor 105 may receive the first instruction. The first instruction may be an operation instruction input by the user through the touch screen or an external input device, or a control instruction input by the user through the voice.

In step 202, a target imaging mode may be determined from the preset imaging modes in response to the first instruction. The preset imaging modes may include a first contrast enhanced imaging mode and a second contrast enhanced imaging mode. The frame rate of the first contrast enhanced imaging mode may be different from the frame rate of the second contrast enhanced imaging mode.

In this embodiment, the processor 105 may determine the target imaging mode from the preset imaging modes in responds to the first instruction. Generally, the preset imaging modes may mainly include two imaging modes, namely the first contrast enhanced imaging mode and the second contrast enhanced imaging mode. The target imaging mode may be the first contrast enhanced imaging mode or the second contrast enhanced imaging mode.

It can be understood that the frame rate of the first contrast enhanced imaging mode may be different from the frame rate of the second contrast enhanced imaging mode. For example, the frame rate of the first contrast enhanced imaging mode may be 10 frames per second (fps) to 15 fps, while the frame rate of the second contrast enhanced imaging mode may be 50 fps to 200 fps. In practical applications, the frame rate of the first contrast enhanced imaging mode and the frame rate of the second contrast enhanced imaging mode may be set, which will not be limited to those above.

In step 203, the ultrasound waves may be transmitted to the target object and the ultrasound echoes returned from the target object may be received according to the determined target imaging mode, so as to obtain the ultrasound echo signals.

In this embodiment, the processor 105 may transmit the ultrasound waves to the target object according to the determined target imaging mode and receive the ultrasound echoes returned from the target object. Alternatively, the processor 105 may transmit the ultrasound waves to the target object according to the determined target imaging mode, and receive the ultrasound echoes returned from the target object according to the target imaging mode. Alternatively, the processor 105 may transmit the ultrasound waves to the target object, and receive the ultrasound echoes returned from the target object according to the target imaging mode. The ultrasound echo signals may be obtained thereby.

It should be noted that the target object may refer to the physiological structure to be examined, such as the liver, the heart, the stomach, or the spleen, etc., which will not be limited herein.

In step 204, the contrast enhanced image may be generated according to the ultrasound echo signals.

In this embodiment, the processor 105 may generate the contrast enhanced images according to the obtained ultrasound echo signals.

In the technical solutions provided by the embodiments of the present disclosure, with the processor 105, the ultrasound imaging device 10 may transmit ultrasound waves to the target object according to the imaging mode selected by the user and receive ultrasound echoes returned from the target object to obtain the echo signals to generate the contrast enhanced images. This way, the imaging mode can be selected according to the diagnosis needs, and the contrast enhanced images may be generated according to the imaging mode. Therefore, the contrast enhanced imaging methods are more flexible, and more accurate or satisfactory contrast enhanced images may be obtained, thereby reducing the difficulty of the diagnosis of the disease. For example, for the contrast enhanced imaging to conventional diseases, the first contrast enhanced imaging mode (e.g., the frame rate is set to 10 fps to 15 fps) may be selected to perform the contrast enhanced imaging. For the contrast enhanced imaging to specific diseases (such as "small lesion with rich blood" with a size of less than 1 cm×1 cm×1 cm), high frame rate mode may be selected to perform the contrast enhanced imaging in order to capture the complete perfusion process, such as the second contrast enhanced imaging mode (e.g., the frame rate is set to 50 fps to 200 fps and there are multiple adjustable frame rates).

Optionally, based on the embodiment of FIG. 2 above, in one optional embodiment of the contrast enhanced imaging method, the first contrast enhanced imaging mode may be pre-configured with a fixed frame rate, where the pre-configured fixed frame rate of the first contrast enhanced imaging mode may be smaller than the frame rate of the second contrast enhanced imaging mode.

In this embodiment, the difference between the first contrast enhanced imaging mode and the second contrast enhanced imaging mode is described. The first contrast enhanced imaging mode may be pre-configured with a fixed frame rate, and the pre-configured fixed frame rate of the first contrast enhanced imaging mode may be smaller than the frame rate of the second contrast enhanced imaging mode.

Figure 3:
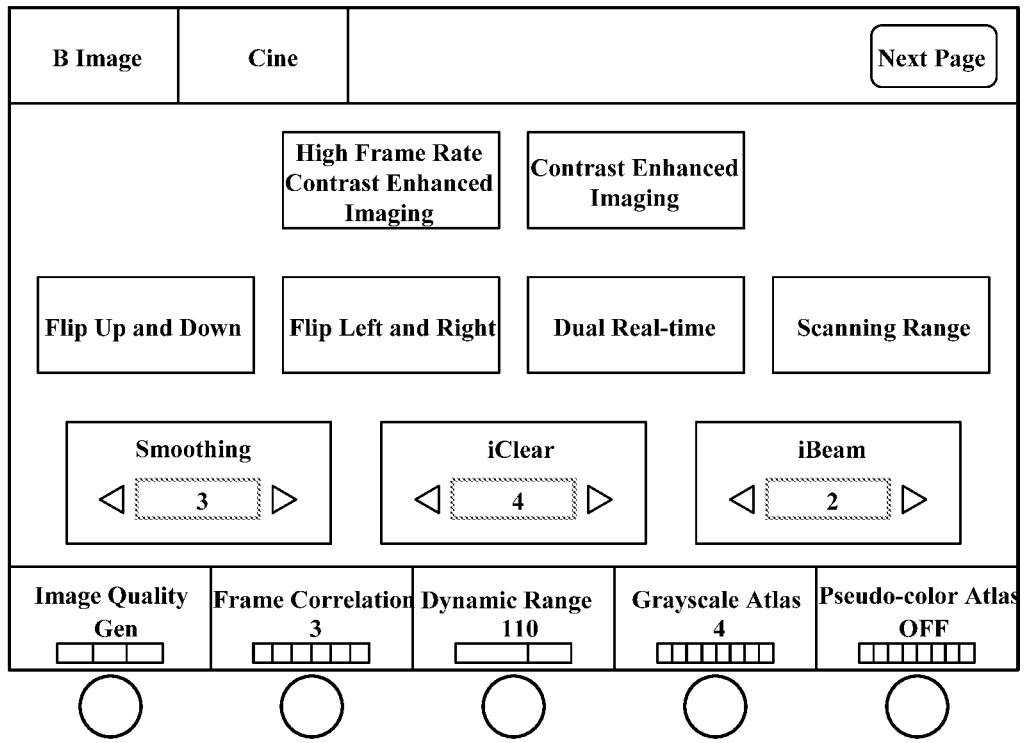
FIG. 3 is a schematic diagram of a main operation interface of the ultrasound imaging device in one embodiment of the present disclosure.

FIG. 3 is a schematic diagram of a main operation interface of the ultrasound imaging device in one embodiment of the present disclosure. As shown in FIG. 3, the interface may include the first contrast enhanced imaging mode and the second contrast enhanced imaging mode. In addition, the interface may also include other modules. Detailed description will be provided below.

"B image" module: when this button is clicked, it may mean that the ultrasound imaging device 10 is in the two-dimensional gray-scale imaging mode, and the operation interface may stay at the "main operation interface".

"Cine" module: when this button is clicked, the playback setting interface may be entered, on which the start frame, the end frame, the playback rate or other parameters for playing the cine loop may be set.

Figure 4A:
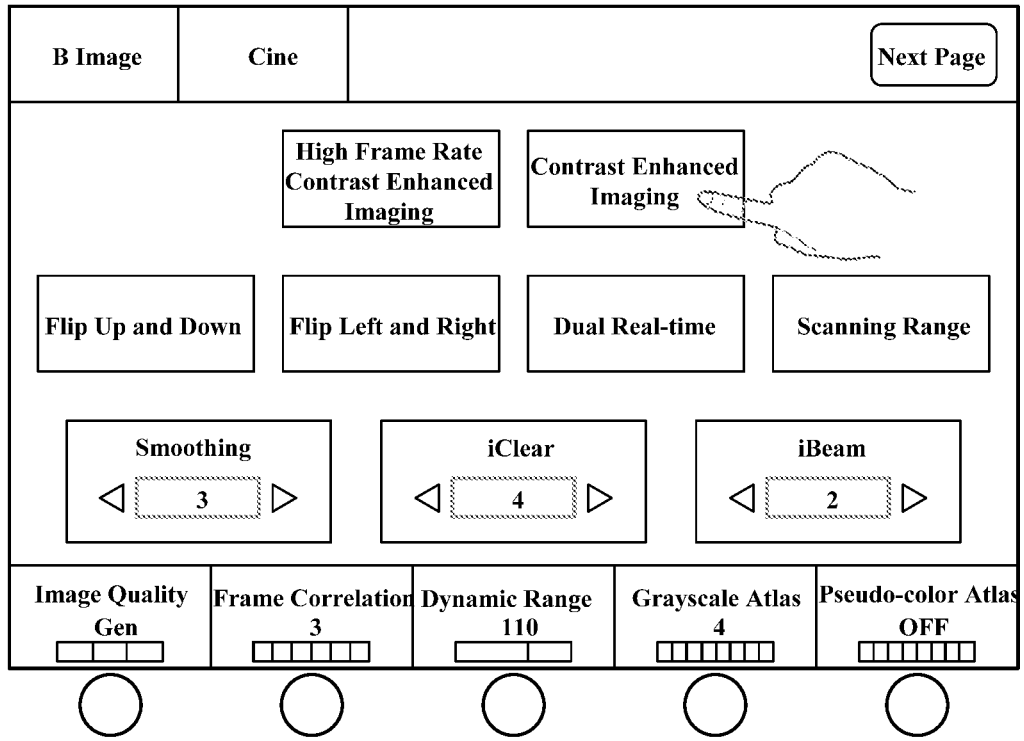
FIG. 4 (a) is a schematic diagram of an interface for selecting the first contrast enhanced imaging mode in one embodiment of the present disclosure.
Figure 4B:
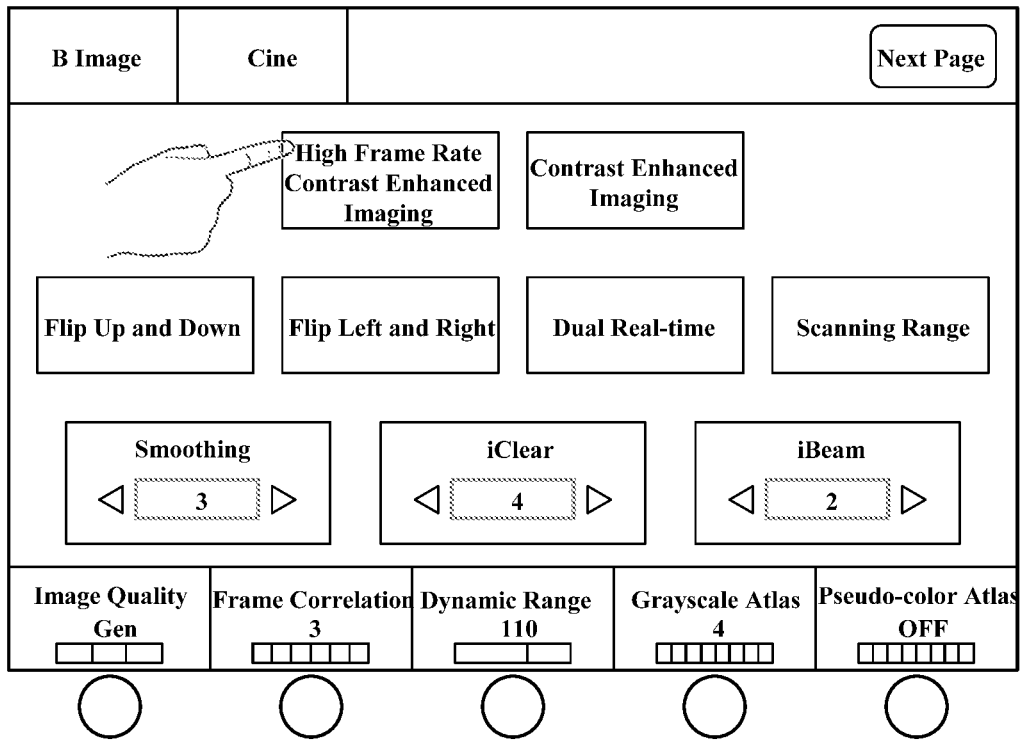

"Contrast enhanced imaging" module: as shown in FIG. 4 (a) which is a schematic diagram of the interface for selecting the first contrast enhanced imaging mode in the embodiment of the present disclosure, the first contrast enhanced imaging mode may be entered when this button is clicked, i.e. the conventional imaging mode.

"High frame rate contrast enhanced imaging" module: as shown in FIG. 4 (b) which is a schematic diagram of an interface for selecting the second contrast enhanced imaging mode in the embodiment of the present disclosure, when this button is clicked, the second contrast enhanced imaging mode may be entered, i.e., the high-frame rate contrast enhanced imaging mode.

"Flip up and down" module: when this button is clicked, the mirror symmetry processing of the image in the vertical direction may be performed.

"Flip left and right" module: when this button is clicked, the mirror symmetry processing of the image in the horizontal direction may be performed.

"Dual real-time" module: when this button is clicked, the dual-image state in two-dimensional grayscale imaging mode may be entered, which is mainly used to compare the effect before and after the parameter adjustment. For example, the left image may be the image before the parameter adjustment while the right image may be the image after the parameter adjustment. Alternatively, the right image may be the image before the parameter adjustment while the left image may be the image after the parameter adjustment.

"Scan/imaging range (FOV)" module: when this button is clicked, the trackball may be operated to control the lateral imaging range, which can be expanded or contracted.

"Smoothing" module: it may be the image smoothing module, which can control the smoothness of the image by adjusting the parameter. The minimum value of the parameter may be 0 (indicating that no smoothing is performed), and the maximum value is any positive integer (which can be set and typically be 6). The smoothness of the image is proportional to this parameter.

"iClear" module: it may be an image enhancement module, which has several image enhancement styles for selection. When "0" is selected, it may mean that no image enhancement processing is performed. When any positive integer n is selected, it may mean that the $n^{th}$ enhancement style is adopted. It may be understood that the value of the parameter of this module here may not correspond to the degree of the image enhancement.

"iBeam" module: it may be the spatial compounding module, in which the multi-angle transmitting and the receiving compounding may be used to improve the signal-to-noise ratio and the spatial resolution of the image, and reduce the black holes. The value of the parameter of this module may correspond to the degree of the spatial compounding. The larger the value, the more the number of transmitting angles and the number of compounding, and vice versa.

"Image quality" module: usually there may be 6 levels for the image quality in the two-dimensional grayscale imaging mode: Pen, Gen, Res, HPen, HGen and HRes. The first three may correspond to the fundamental mode and be respectively focused on penetration, general and resolution. The latter three may correspond to the harmonic mode and similarly be respectively focused on penetration, general and resolution. It can be understood that the above are only typical settings, and the number of the levels and the emphasis of each level can be set as required.

"Frame correlation" module: it can reduce the background noise. The minimum value of the parameter may be 0 and the maximum value of the parameter may be any positive integer (which can be set, and currently typically be 6). The value of the parameter of this module may be proportional to the degree of the frame correlation.

"Dynamic range" module: it may be the dynamic range adjustment module of the image. The larger the value, the larger the dynamic range of the image, and vice versa.

"Grayscale Atlas" module: it may be used to adjust the grayscale of the image. The value of the parameter of this module may not correspond to the degree of the adjustment, but correspond to different grayscale types.

"Pseudo-color atlas" module: it may be used to adjust the pseudo-color of the image. The value of the parameter of this module may not correspond to the degree of the adjustment, but correspond to different pseudo-color types.

In the embodiment of the present disclosure, the difference between the first contrast enhanced imaging mode and the second contrast enhanced imaging mode has been described, that is, the pre-configured fixed frame rate of the first contrast enhanced imaging mode may be smaller than the frame rate of the second contrast enhanced imaging mode. In this way, the ultrasound imaging device 10 can provide two contrast enhanced imaging modes with different frame rates, such that the user can select a contrast enhanced imaging mode according to diagnostic needs. Therefore, the contrast enhanced imaging mode can be more flexible and more accurate or satisfactory contrast enhanced images may be obtained, thereby reducing the difficulty in diagnosing the disease.

Optionally, based on the embodiment in FIG. 2 above, in one embodiment of the contrast enhanced imaging method, the first contrast enhanced imaging mode may be pre-configured as a first imaging parameter, and the second contrast enhanced image mode may be pre-configured as a second imaging parameter.

The first imaging parameter may include at least one of: a first number of transmitting, a first line density, a first imaging range and a first pulse repetition frequency.

The second imaging parameter may include at least one of: a second number of transmitting, a second line density, a second imaging range and a second pulse repetition frequency.

The first number of transmitting may be greater than the second number of transmitting, the first line density may be greater than the second line density, the first imaging range may be greater than the second imaging range, and the first pulse repetition frequency may be lower than the second pulse repetition frequency.

In this embodiment, the first imaging parameter pre-configured for the first contrast enhanced imaging mode and the second imaging parameter pre-configured for the second contrast enhanced imaging mode have been specifically introduced.

Specifically, the first imaging parameter may include at least one of: a first number of transmitting, a first line density, a first imaging range and a first pulse repetition frequency (PRF). The second imaging parameter may include at least one of: a second number of transmitting, a second line density, a second imaging range and a second pulse repetition frequency. It should be noted that when adjusting the first imaging parameter and the second imaging parameter, at least one of the following conditions may be satisfied:

(1) the first number of transmitting is greater than the second number of transmitting;
(2) the first line density is greater than the second line density;
(3) the first imaging range is greater than the second imaging range; and
(4) the first PRF is lower than the second PRF.

The four conditions above may also be optional conditions for achieving a high frame rate. For example, plane wave transmission technology or coherence transmission synthesis (CTS) technology may be used to reduce the number of transmittings. It can reduce the line density while ensuring the image quality. The FOV can be reduced after the lesion is positioned. After positioning the lesion, a specific region of interest (ROI) may be selected and the PRF may be increased.

In one embodiment, different contrast enhanced imaging modes may be obtained by adjusting the imaging parameters, and either the first number of transmitting being greater than the second number of transmitting or the first line density being greater than the second line density or the first imaging range being greater than the second imaging range or the first PRF being lower than the second PRF can improve the frame rate. Therefore, it has strong feasibility and reliability.

Optionally, based on the embodiment in to FIG. 2 above, in one embodiment of the contrast enhanced imaging method, when it is determined that the target imaging mode is the first contrast enhanced imaging mode, the following steps will be performed.

The processor 105 may transmit the ultrasound waves to the target object and receive ultrasound echoes returned from the target object to obtain the ultrasound echo signals according to the determined target imaging mode, which may include:

the processor 105 transmitting the ultrasound waves to the target object and receiving the ultrasound echoes returned from the target object to obtain the first ultrasound echo signals according to the first imaging parameters;

The processor 105 may generate the contrast enhanced image according to the ultrasound echo signals, which may include:

the processor 105 generating a first contrast enhanced image according to the first ultrasound echo signals.

In this embodiment, when the target imaging mode is the first contrast enhanced imaging mode, the contrast enhanced imaging may be performed with a fixed frame rate. The processor 105 may transmit the ultrasound waves to the target object according to the determined first contrast enhanced imaging mode, and then receive the ultrasound echoes returned from the target object. Alternatively, the processor 105 may transmit the ultrasound waves to the target object according to the determined first contrast enhanced imaging mode, and then receive the ultrasound echoes returned from the target object according to the first contrast enhanced imaging mode. Alternatively, the processor 105 may transmit ultrasound waves to the target object, and receive the ultrasound echoes returned from the target object according to the first contrast enhanced imaging mode. This way, the first ultrasound echo signals may be obtained. The first contrast enhanced image may be generated according to the first ultrasound echo signals.

Further, in one embodiment of the present disclosure, in the first contrast enhanced imaging mode, the ultrasound ways may be transmitted to the target object and the ultrasound echoes returned from the target object may be received according to the first imaging parameter to obtain the first ultrasound echo signals, and the first contrast enhanced image may be generated according to the first ultrasound signals. In this way, in the case that the high frame rate imaging is not necessary the fixed frame rate may be used to obtain the contrast enhanced images, thereby improving the flexibility and operability of the contrast enhanced imaging.

Optionally, based on the embodiment in FIG. 2 above, in one embodiment of the contrast enhanced imaging method, when it is determined that the target imaging mode is the second contrast enhanced imaging mode, the following steps will be performed.

The processor 105 may transmit the ultrasound waves to the target object and receive the ultrasound echoes returned from the target object to obtain the ultrasound echo signals according to the determined target imaging mode, which may include:

the processor 105 transmitting the ultrasound waves to the target object and receiving the ultrasound echoes returned from the target object to obtain a second ultrasound echo signal according to the second imaging parameter.

The processor 105 may generate the contrast enhanced image according to the ultrasound echo signal, which may include:

the processor 105 generating a second contrast enhanced image according to the second ultrasound echo signal.

In this embodiment, in the case that the target imaging mode is the second contrast enhanced imaging mode, a high frame rate may be used for contrast enhanced imaging. The processor 105 may transmit ultrasound waves to the target object according to the determined second contrast enhanced imaging mode (for example, during the transmitting, the number of ultrasound wave transmittings may be reduced or the PRF may be increased so as to increase the frame rate), and receive the ultrasound echoes returned from the target object. Alternatively, the processor 105 may transmit the ultrasound waves to the target object according to the determined second contrast enhanced imaging mode, and receive the ultrasound echoes returned from the target object also according to the second contrast enhanced imaging mode. Alternatively, the processor 105 may transmit the ultrasound waves to the target object, and receive the ultrasound echoes returned from the target object according to the second contrast enhanced imaging mode (for example, during the receiving, the line density or the imaging range may be reduced so as to improve the frame rate). This way, the second ultrasound echo signal may be obtained. The second contrast enhanced image may be generated according to the second ultrasound echo signal.

In the embodiment of the present disclosure, in the second contrast enhanced imaging mode, the ultrasound waves may be transmitted to the target object and the ultrasound echoes returned from the target object may be received according to the second imaging parameter to obtain the second ultrasound echo signal, and the second contrast enhanced image may be generated according to the second ultrasound echo signal. In this way, a fully automatic and variable high frame rate imaging may be achieved during the contrast enhanced imaging. Therefore, the manual operation is not necessary and the user can pay more attention on scanning and observing the perfusion in the lesion.

Optionally, based on the embodiments in FIG. 2 above, in one embodiment of the contrast enhanced imaging method provided by present disclosure, the second contrast enhanced imaging mode may be pre-configured with at least two frame rates and each frame rate may have corresponding imaging parameters. In the case that it is determined that the target imaging mode is the second contrast enhanced imaging mode, the processor 105 may also perform the following steps.

A second instruction may be received.

In response to the second instruction, a target frame rate may be determined from the at least two frame rates.

Transmitting the ultrasound waves to the target object according to the determined target imaging mode and receiving the ultrasound echoes returned from the target object to obtain the ultrasound echo signals may include:

transmitting the ultrasound waves to the target object and receive the ultrasound echoes returned from the target object to obtain the ultrasound echo signal according to the imaging parameters pre-configured according to the target frame rate.

In this embodiment, when it is determined that the target imaging mode is the second contrast enhanced imaging mode, the processor 105 may receive the second instruction input by the user, and, in response to the second instruction, determine the target frame rate from the at least two frame rates. The second instruction here may be a manual frame rate setting instruction or an automatic frame rate setting instruction.

Figure 5:
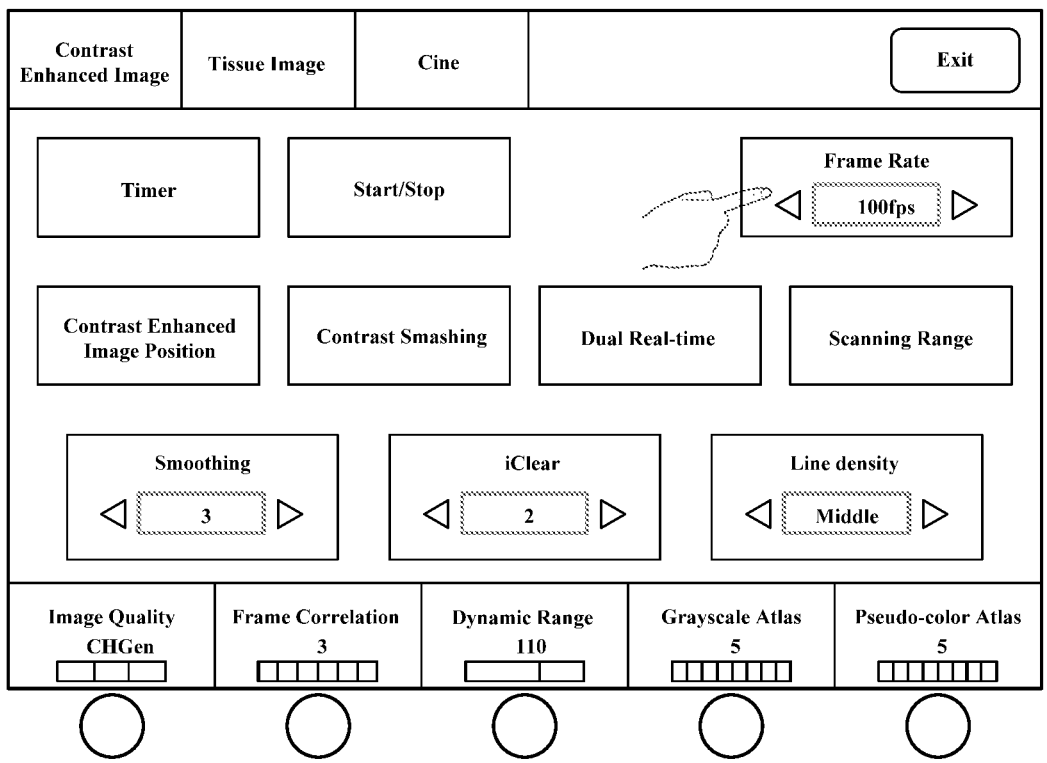
FIG. 5 is a schematic diagram of an interface for manually determining the target frame rate in one embodiment of the present disclosure.

FIG. 5 is a schematic diagram of an interface for manually determining the target frame rate in one embodiment of the present disclosure. As shown in FIG. 5, there are several modules in the interface in FIG. 5 which have the same name with the modules in the interface in FIG. 3. In order to avoid redundancy, only the modules with different functions and name from FIG. 3 will be described here.

"Contrast enhanced image" module: when this button is clicked, the parameters in the interface related to the contrast enhanced image may be in an adjustable state.

"Tissue image" module: when this button is clicked, the parameters in the interface related to the tissue image may be in an adjustable state.

"Timer" module: it is the timer in the high frame rate contrast enhanced imaging mode (i.e., the second contrast enhanced imaging mode).

"Start/Stop" module: it may be a button for starting and stopping saving the high-frame rate contrast enhanced cine loop.

"Frame rate" module: it may be module for controlling the frame rate in the high-frame rate contrast enhanced imaging mode. The value of the parameter may correspond to the frame rate. The larger the value, the higher the frame rate.

"Contrast enhanced image position" module: it may be a module which controls whether the contrast enhanced image is on the left or on the right in dual-frame mode.

"Contrast smashing" module: when this button is clicked, it may mean that the ultrasound imaging device 10 is in a state of smashing contrast agent, which is mainly used to remove the residual microbubbles at the scanning site.

"Dual real-time" module: unlike the "dual real-time" module in FIG. 3, the "dual real-time" module here may refer only to the dual-frame state in the contrast enhanced imaging mode, that is, the contrast enhanced image and the tissue image are displayed simultaneously in the imaging area. Usually they may be arranged in left and right. For example, the tissue image may be on the left and the contrast enhanced image may be on the right. The positions of them may be exchanged by operating the "contrast enhanced image position" button.

"Image quality" module: it may be an image quality module in contrast enhanced imaging mode. There may usually be three levels: CHPen, CHGen and CHRes, which may respectively focused on penetration, general and resolution. The above are only typical settings. The number of the levels and the emphasis of each level may be set.

Figure 6:
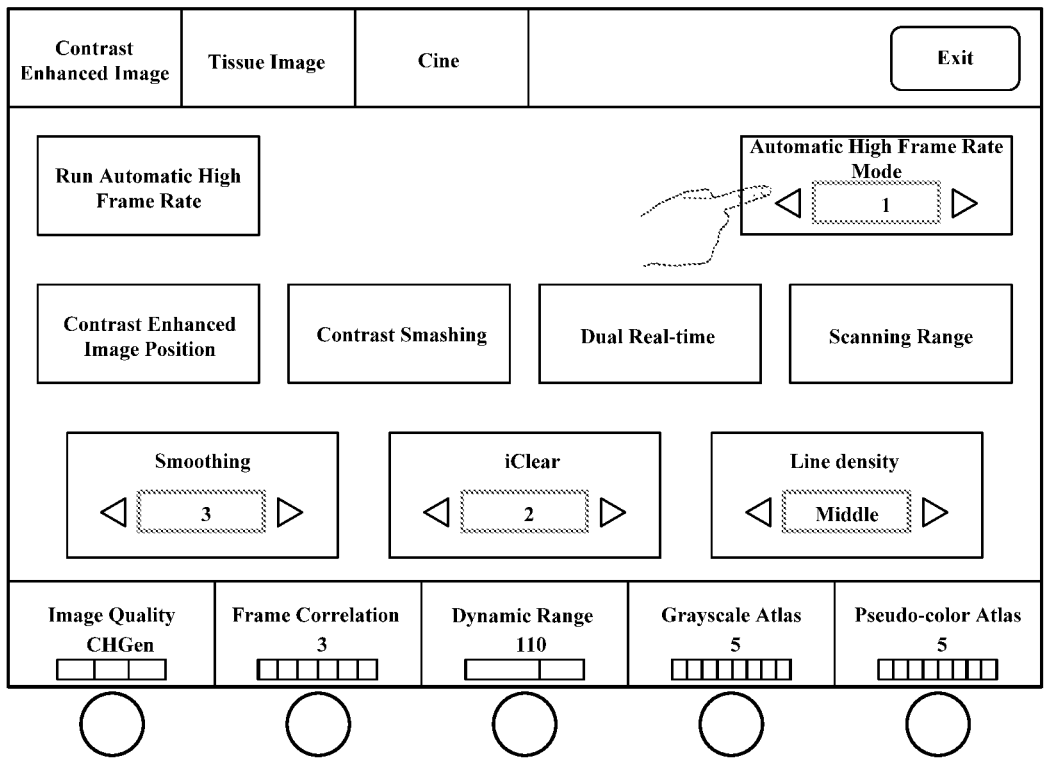
FIG. 6 is a schematic diagram of an interface for automatically determining the target frame rate in one embodiment of the present disclosure.

In addition, in one embodiment, the target frame rate may be automatically determined. Referring to FIG. 6 which is a schematic diagram of an interface for automatically determining the target frame rate in one embodiment of the present disclosure, when the user clicks "automatic high frame rate imaging mode", the processor 105 may execute step 202 to select the target frame rate from the preset frame rates.

After the user selects the target frame rate, the processor 105 will transmit the ultrasound waves to the target object and receive the ultrasound echoes returned from the target object to obtain the ultrasound echo signals according to the pre-configured imaging parameters corresponding to the target frame rate.

In the embodiments of the present disclosure, the user can flexibly set the target frame rate according to actual needs, and the ultrasound imaging device can generate the contrast enhanced images according to the target frame rate set by the user. Therefore, the flexibility and feasibility of the solutions are increased, and the user can pay more attention on scanning and observing the perfusion in the lesion.

Optionally, based on the embodiments in FIG. 2 above, in one embodiment of the contrast enhanced imaging method provided by the present disclosure, the second contrast enhanced imaging mode may be pre-configured with at least two frame rates and the execution sequence of the at least two frame rates. Each frame rate may be pre-configured with corresponding imaging parameters and imaging duration. When the target imaging mode is determined to be the second contrast enhanced imaging mode, the processor 105 may also execute the follows steps.

A third instruction may be received.

Transmitting the ultrasound waves to the target object and receiving the ultrasound echoes returned from the target object to obtain the ultrasound echo signals according to the determined target imaging mode may include:

in response to the third instruction, sequentially transmitting the ultrasound waves to the target object and receiving the ultrasound echoes returned from the target object to obtain the ultrasound echo signals according to the execution sequence, the imaging parameters pre-configured for the frame rates and the imaging duration.

The processor 105 may generate the contrast enhanced image according to the ultrasound echo signal, which may include:

the processor 105 sequentially generating the contrast enhanced images according to the obtained corresponding ultrasound echo signals.

In this embodiment, the user may also configure the second contrast enhanced imaging mode according to the actual needs. Specifically, the user can configure the at least two frame rates and the execution sequence of at least two frame rates.

Figure 7:
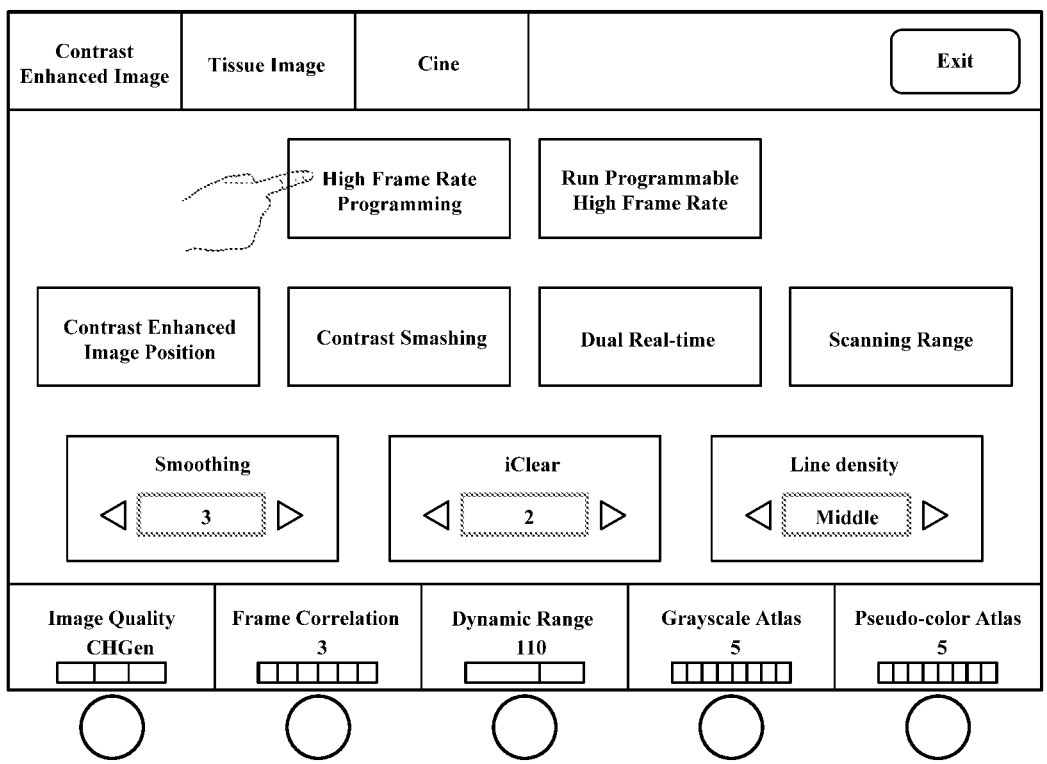
FIG. 7 is a schematic diagram of an interface for the programmable high frame rate contrast enhanced imaging in one embodiment of the present disclosure.

Referring to FIG. 7 which is a schematic diagram of an interface for the programmable high frame rate contrast enhanced imaging in one embodiment of the present disclosure, after clicking the "high frame rate programming" module, the user may be enabled to set the high frame rate parameters, that is, configure the second contrast enhanced imaging mode. The configurable content may be shown in FIG. 8, which is a schematic diagram of an interface for setting the high frame rate parameters in one embodiment of the present disclosure, where "1", "2" and "3" may be the execution sequences, that is, the contrast enhanced images may be generated according to the order of "1", "2" and "3". The imaging duration may represent the length of time from transmitting the ultrasound waves, receiving the ultrasound echo signals to generating the contrast enhanced image according to the ultrasound echo signals. The start time and the end time may be the start time and the end time of generating the contrast enhanced image, and the frame rate may indicate the value of the frame rate of the generated contrast enhanced images.

Figure 8:
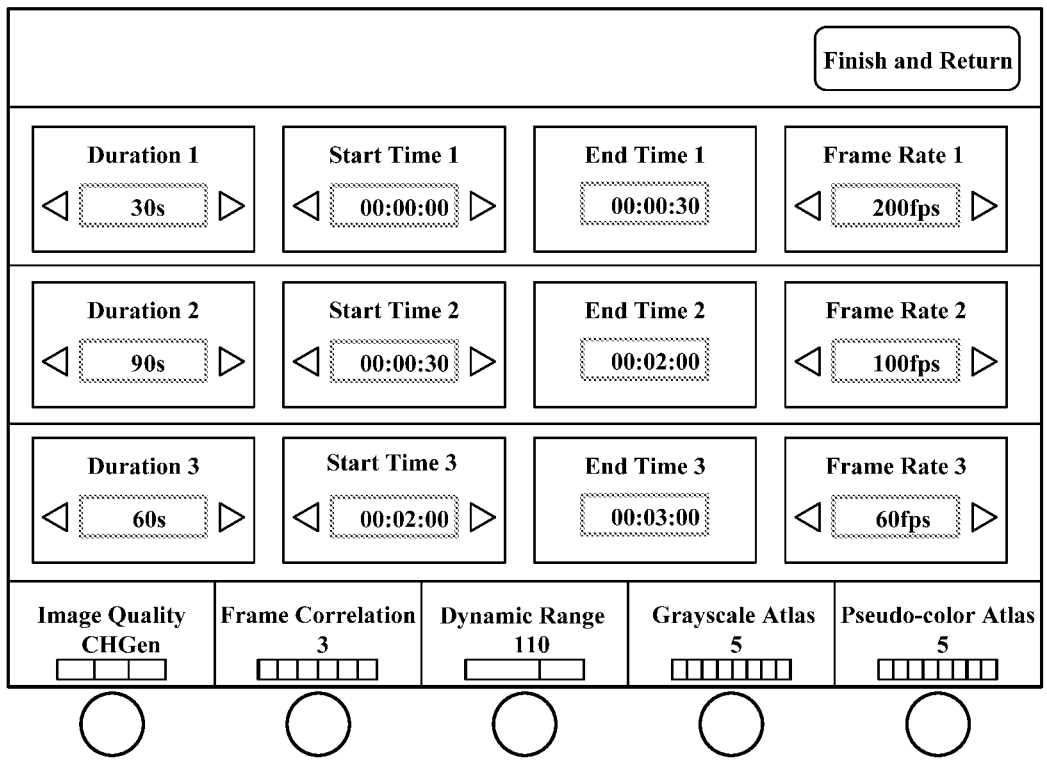
FIG. 8 is a schematic diagram of an interface for setting the high frame rate parameter in one embodiment of the present disclosure.

It should be noted that, in order to describe the technical solutions more intuitively, FIG. 8 only provides a special case where there are 3 high frame rate fragments. In the actual implementation, the number of the high frame rate fragments may be any integer greater than 1, which will not be limited herein.

After the configuration is completed, a third instruction input by the user may be received. The processor 105 may, in response to the third instruction, sequentially transmit the ultrasound waves to the target object and receive the ultrasound echoes returned from the target object to obtain the ultrasound echo signals according to the execution sequence, the imaging parameters pre-configured for the frame rate and the imaging duration. The contrast enhanced images may be sequentially generated according to the obtained ultrasound echo signals.

In the embodiments of the present disclosure, the user can personalize the high-frame rate contrast enhanced imaging in advance, and achieve the fully automatic and variable high-frame rate contrast enhanced imaging without manual operation, thereby improving the practicality and feasibility of the solutions.

Optionally, based on the embodiments corresponding to FIG. 2 above, in one embodiment of the contrast enhanced imaging method provided by the present disclosure, the imaging parameter may includes at least one of: the number of transmitting, the line density, the imaging range and the pulse repetition frequency.

In this embodiment, when configuring the imaging parameters, at least one of the number of transmittings, the line density, the imaging range and the PRF may be considered. Reducing the number of transmittings or shortening the receiving time can increase the frame rate. Reducing the line density to increase the number of the image frames can increase the frame rate. In addition, after positioning the lesion, reducing the FOV or increasing the PRF can also increase the frame rate.

In the embodiments of the present disclosure, different contrast enhanced imaging modes may be set by the adjustment of the imaging parameter. Therefore, it will have strong feasibility and reliability.

Optionally, based on the embodiments above corresponding to FIG. 2, in one embodiment of the contrast enhanced imaging method provided by the present disclosure, the processor 105 may also perform the following steps.

A fourth instruction may be received.

In response to the fourth instruction, the transmitting of the ultrasound waves to the target object and the receiving of the ultrasound echoes returned from the target object may be stopped.

In this embodiment, the fourth instruction input by the user may be received, and, in response to the fourth instruction, the transmitting of the ultrasound waves to the target object and the receiving of the ultrasound echoes returned from the target object may be stopped.

Therefore, in the embodiments of the present disclosure, the user can customize the frame rate and can start or stop the contrast enhanced imaging mode at any time, thereby improving the practicality and flexibility of the solutions.

Figure 9:
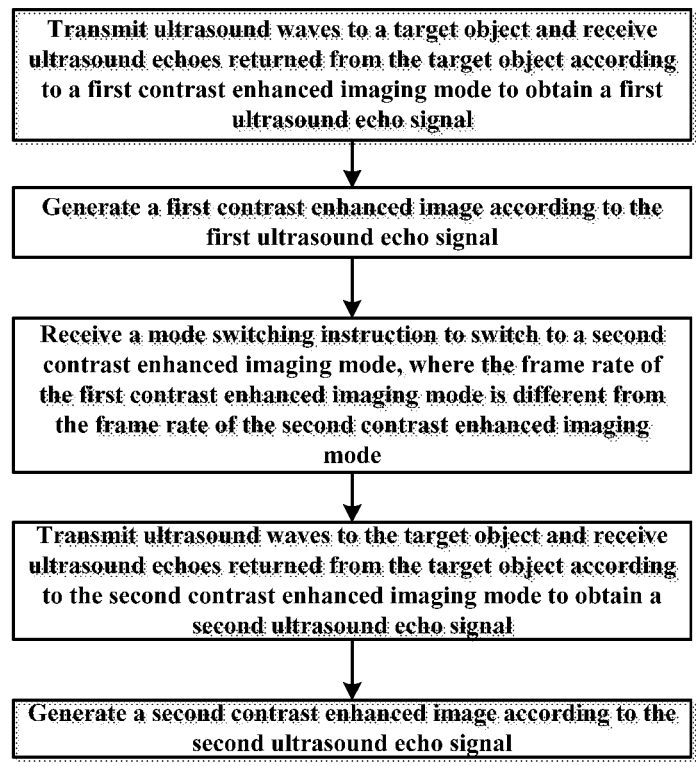
FIG. 9 is a schematic flowchart of the contrast enhanced imaging method in another embodiment of the present disclosure.

The contrast enhanced imaging methods in the present disclosure will be described in detail below. Referring to FIG. 9, in one embodiment, a contrast enhanced imaging method is provided. This method may be applied in the ultrasound imaging device, and particularly suitable for the ultrasound imaging device including the touch screen in which the touch operstion may be used to input the instructions. The ultrasound imaging device may be used to generate the contrast enhanced images. In one embodiment, the contrast enhanced imaging method may include the following steps.

In step 301, the ultrasound waves may be transmitted to the target object and the ultrasound echoes returned from the target object may be received to obtain the first ultrasound echo signal according to the first contrast enhanced imaging mode.

In this embodiment, the processor 105 may transmit the ultrasound waves to the target object and receive the ultrasound echoes returned from the target object to obtain the first ultrasound echo signal according to the first contrast enhanced imaging mode.

The processor 105 may transmit the ultrasound waves to the target object according to the determined first contrast enhanced imaging mode, and receive the ultrasound echoes returned from the target object to obtain the first ultrasound echo signal. Alternatively, the processor 105 may transmit the ultrasound waves to the target object according to the determined first contrast enhanced imaging mode and receive the ultrasound echoes returned from the target object according to the first contrast enhanced imaging mode to obtain the first ultrasound echo signal. Alternatively, the processor 105 may transmit the ultrasound waves to the target object, and receive the ultrasound echoes returned from the target object according to the first contrast enhanced imaging mode to obtain the first ultrasound echo signal.

It should be noted that the target object herein may be the physiological structure to be examined, such as the liver, the heart, the stomach, or the spleen, etc., which will not be limited herein.

In step 302, the first contrast enhanced image may be generated according to the first ultrasound echo signal.

In this embodiment, the processor 105 may generate the first contrast enhanced image according to the obtained first ultrasound echo signal.

In step 303, a mode switching instruction may be received to switch to the second contrast enhanced imaging mode, where the frame rate of the first contrast enhanced imaging mode may be different from the frame rate of the second contrast enhanced imaging mode.

In this embodiment, the processor 105 may receive the mode switching instruction input by the user, and switch the first contrast enhanced imaging mode to the second contrast enhanced imaging mode according to the mode switching instruction. Thereafter, the ultrasound waves may be transmitted to the target object and the ultrasound echoes returned from the target object may be obtained according to the second contrast enhanced imaging mode to obtain the second ultrasound echo signal.

It can be understood that the frame rate of the first contrast enhanced imaging mode and the frame rate of the second contrast enhanced imaging mode may be different. For example, the frame rate of the first contrast enhanced imaging mode may be 10 fps to 15 fps, and the frame rate of the second contrast enhanced imaging mode may be 50 fps to 200 fps. In practical applications, the frame rate of the first contrast enhanced imaging mode and the frame rate of the second contrast enhanced imaging mode may also be set, which will not be limited herein.

In step 304, the ultrasound waves may be transmitted to the target object and the ultrasound echoes returned from the target object may be obtained according to the second contrast enhanced imaging mode to obtain the second ultrasound echo signal.

In this embodiment, the processor 105 may control to transmit the ultrasound waves to the target object according to the determined second contrast enhanced imaging mode and receive the ultrasound echoes returned from the target object to obtain the second ultrasound echo signal. Alternatively, the processor 105 may control to transmit the ultrasound waves to the target object according to the determined second contrast enhanced imaging mode and receive the ultrasound echoes returned from the target object according to the second contrast enhanced imaging mode to obtain the second ultrasound echo signal. Alternatively, the processor 105 may control to transmit the ultrasound waves to the target object and receive the ultrasound echoes returned from the target object according to the determined second contrast enhanced imaging mode to obtain the second ultrasound echo signal.

In step 305, the second contrast enhanced image may be generated according to the second ultrasound echo signal.

In this embodiment, the processor 105 may generate the second contrast enhanced image according to the obtained second ultrasound echo signal.

In the technical solutions provided by the present disclosure, the processor 105 may control, according to the imaging mode selected by the user, to transmit the ultrasound waves to the target object and receive the ultrasound echoes returned from the target object to obtain the echo signals to generate the contrast enhanced image. In this way, the imaging mode can be selected according to the diagnosis needs, and the contrast enhanced images may be generated according to the selected imaging mode. Therefore, the contrast enhanced imaging methods are more flexible, and more accurate or satisfactory contrast enhanced images may be obtained, thereby reducing the difficulty in the diagnosis of the disease.

It should be understood that the embodiments of the present disclosure may mainly include three application modes, i.e. the "manual high frame rate contrast enhanced imaging mode", the "automatic high frame rate contrast enhanced imaging mode", and the "programmable high frame rate contrast enhanced imaging mode", which will be described below in connection with the drawings.

Figure 10:
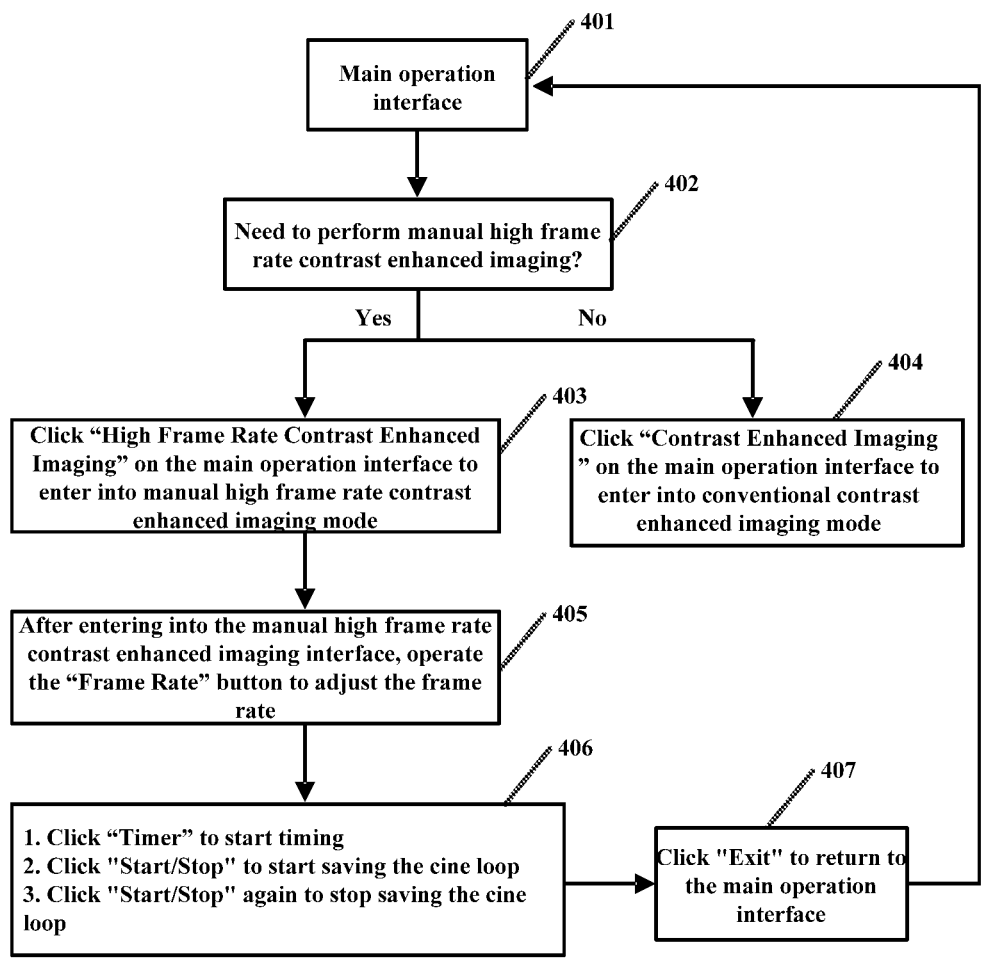
FIG. 10 is a schematic flowchart of the "manual high frame rate contrast enhanced imaging" mode in the applications of the present disclosure.

FIG. 10 is a schematic flowchart of the "manual high frame rate contrast enhanced imaging" mode in one embodiment of the present disclosure, which will be described below.

In step 401, the ultrasound imaging device 10 may enter into the main operation interface.

In step 402, a button may be provided on the main operation interface of the ultrasound imaging device 10 to start or stop the high frame rate contrast enhanced imaging mode at any time. For example, a prompt of "need to perform manual high frame rate contrast enhanced imaging?" may be displayed on the main operation interface. In the case that the user selects "Yes", step 403 will be performed; otherwise, in the case that the user selects "No", step 404 will be performed.

In step 403, after entering the "high frame rate contrast enhanced imaging" mode, the frame rate may be set according to requirements. The lower limit of the frame rate should not be lower than the conventional contrast frame rate. The upper limit of the frame rate will be determined by the system. The user may not change the upper and lower limits.

In step 404, in the case that the manual high-frame rate contrast enhanced imaging is not necessary, the user may click the "contrast enhanced imaging" button on the main operation interface to enter into the conventional contrast enhanced imaging mode.

In step 405, after entering into the manual high frame rate contrast enhanced imaging interface, the frame rate may be adjusted by operating the "frame rate" button.

In step 406, the user may click the "timer" button to start timing, then click the "start/stop" button to start saving the cine loop, and click the "start/stop" button again to stop saving the cine loop.

In step 407, the user may click "exit" to return to the main operation interface of the ultrasound imaging device.

Figure 11:
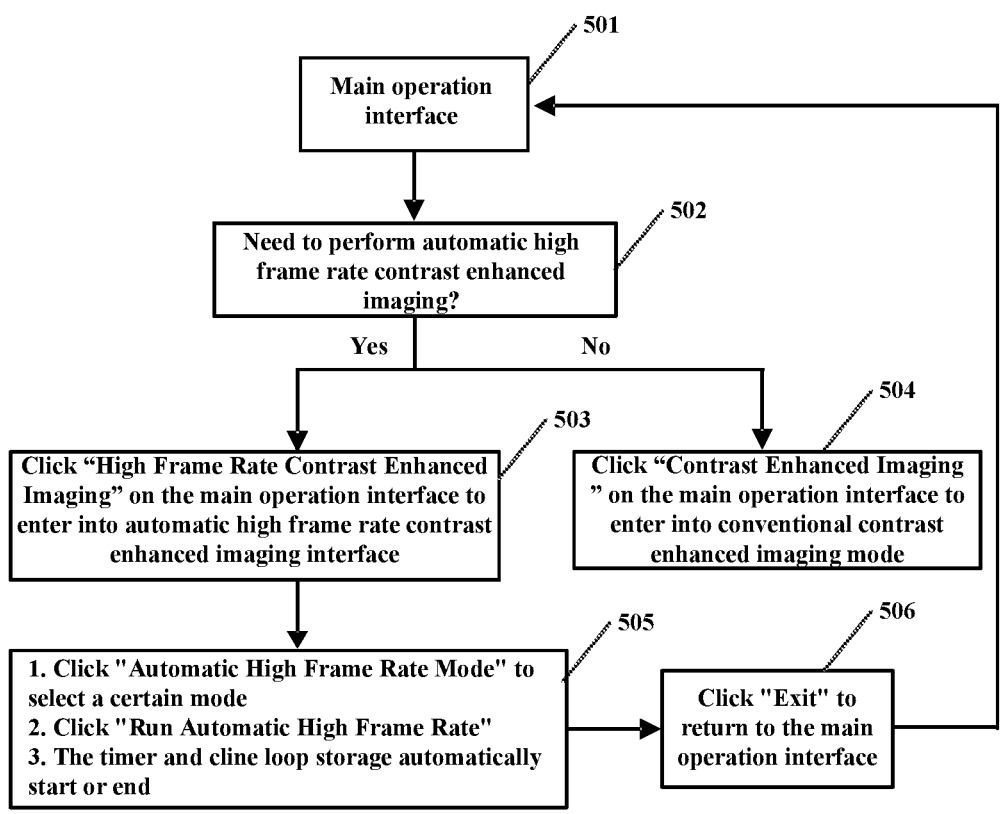
FIG. 11 is a schematic flowchart of the "automatic high frame rate contrast enhanced imaging" mode in the applications of the present disclosure.

FIG. 11 is a schematic flowchart of the "automatic high frame rate contrast enhanced imaging" mode in one embodiment of the present disclosure, which will be described below.

In step 501, the ultrasound imaging device 10 may enter into the main operation interface.

In step 502, a button may be provided on the main operation interface of the ultrasound imaging device 10 to enter into the "automatic high frame rate contrast enhanced imaging" interface. For example, a prompt of "need to perform automatic high frame rate contrast enhanced imaging?" may be displayed on the main operation interface. In the case that the user selects "Yes", step 503 will be performed; otherwise, in the case that the user selects "No", step 504 will be performed.

In step 503, after entering into the "automatic high frame rate contrast enhanced imaging" interface, there are several high frame rate modes for the user to select. After the mode is selected, the "automatic high frame rate contrast enhanced imaging" mode may be started with one click. It may be fully automatic until the contrast enhanced imaging is ended. The parameters in the high frame rate modes, such as the duration of the contrast enhanced imaging, the start/end time, the number of high frame rate clips and the frame rate in each clip, may be written into the device in advance, and the user may not change them.

In step 504, in the case that the automatic high-frame rate contrast enhanced imaging is not necessary, the user may click the "contrast enhanced imaging" button on the main operation interface to enter into the conventional contrast enhanced imaging mode.

In step 505, the user may click "automatic high frame rate mode", and click "run automatic high frame rate" after selecting a mode. In this case, the timer and cline loop storage will automatically start or end.

In step 506, the user may click "exit" to return to the main operation interface of the ultrasound imaging device.

Figure 12:
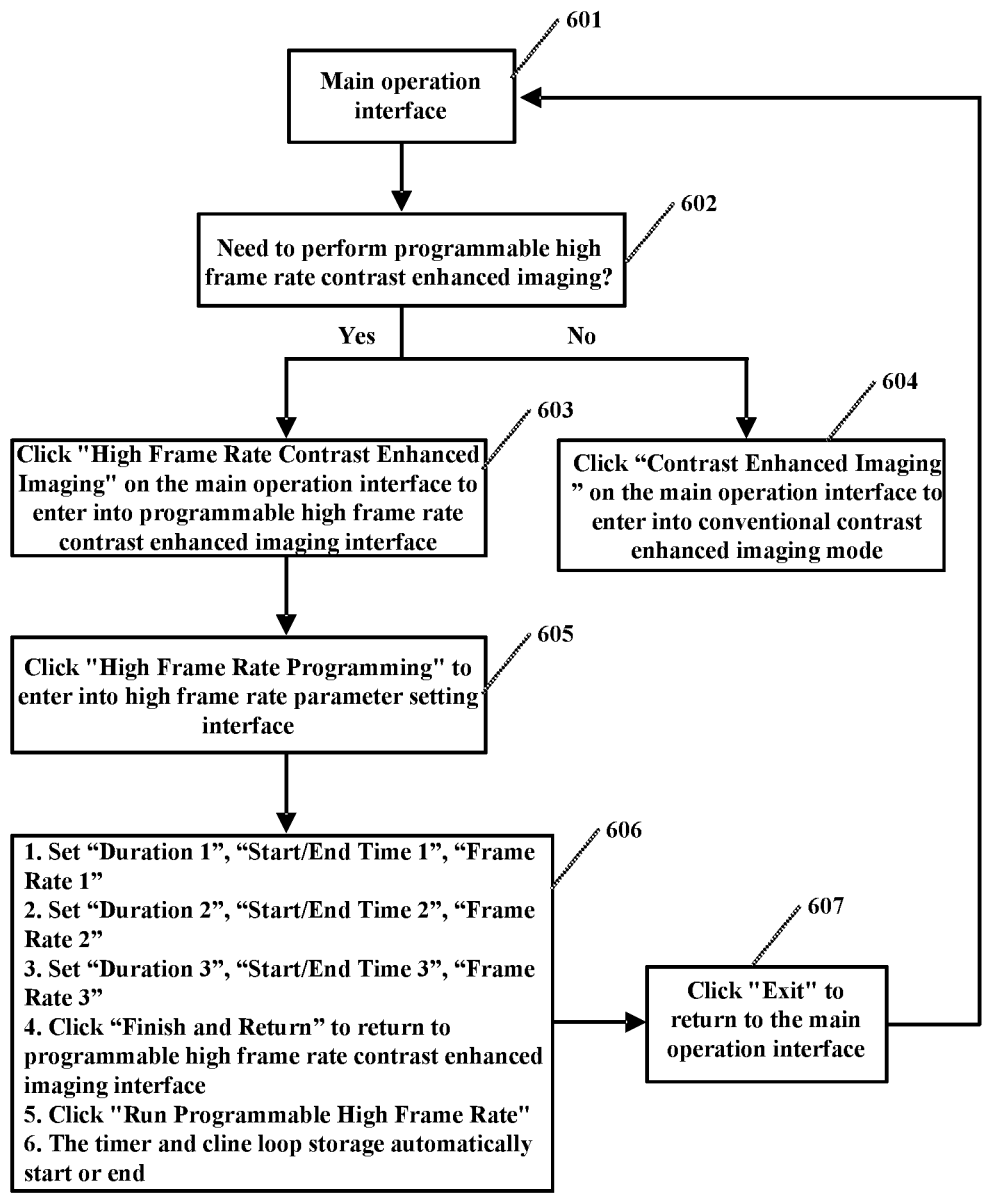
FIG. 12 is a schematic flowchart of the "programmable high frame rate contrast enhanced imaging" mode in the applications of the present disclosure.

FIG. 12 is a schematic flowchart of the "programmable high frame rate contrast enhanced imaging" mode in one embodiment of the present disclosure, which will be described below.

In step 601, the ultrasound imaging device 10 may enter into the main operation interface.

In step 602, a button may be provided on the main operation interface of the ultrasound imaging device 10 to enter into the "programmable high frame rate contrast enhanced imaging" interface. For example, a prompt of "need to perform programmable high frame rate contrast enhanced imaging?" may be displayed on the main operation interface. In the case that the user selects "Yes", step 603 will be performed; otherwise, in the case that the user selects "No", step 604 will be performed.

In step 603, when clicking the "high frame rate contrast enhanced imaging" on the main operation interface, the programmable high frame rate contrast enhanced imaging interface may be entered.

In step 604, in the case that the programmable high-frame rate contrast enhanced imaging is not necessary, the user may click the "contrast enhanced imaging" button on the main operation interface to enter into the conventional contrast enhanced imaging mode.

In step 605, after entering into the "programmable high frame rate contrast enhanced imaging" interface, the high frame rate parameter setting interface may be entered by clicking the "high frame rate programming" button, by which the user may set the parameters such as the duration of the contrast enhanced imaging, the start/end time, the number of the high frame rate clips and the frame rate of the clips, etc. After the setting is completed, it may be returned to the "programmable high frame rate contrast enhanced imaging" interface. The "programmable high frame rate contrast" mode may be started by one click, and may be fully automatic until the end of the contrast enhanced imaging.

In step 606, the "duration", "start/end time" and "frame rate" may be set. After the setting is completed, it may return to the programmable high frame rate contrast enhanced imaging interface by clicking "finish and return". By clicking the "run programmable high frame rate" button, the contrast enhanced imaging may be started, and the timer and the cine loop storage may automatically start or end.

In step 607, the user may click "exit" to return to the main operation interface of the ultrasound imaging device.

The embodiments above may be implemented wholly or partly by software, hardware, firmware or any combination thereof. When implemented by software, they may be implemented wholly or partly in the form of a computer program product.

The computer program product may include one or more computer instructions. When the computer instructions are loaded and executed on the computer, all or part of the processes or functions in the embodiments of the present disclosure may be generated. The computer may be a general-purpose computer, a dedicated computer, a computer network or other programmable devices. The computer instructions may be stored in a computer-readable storage medium or be transferred from one computer-readable storage medium to another computer-readable storage medium. For example, the computer instructions may be transferred from a website site, a computer, a server or a data center to another website, computer, server or data center via a wired (such as coaxial cable, optical fiber, digital subscriber line (DSL)) or wireless (such as infrared, wireless, microwave, etc.) connection. The computer-readable storage medium may be any available medium on which the computer can store data or may include one or more data storage devices integrated with one or more available medium, such as a server, a data center or the like. The available medium may be a magnetic medium (such as a floppy disk, a hard disk, a magnetic tape), an optical medium (such as a DVD), or a semiconductor medium (such as a solid state disk (SSD)), etc.

Those skilled in the art can clearly understand that, for the convenience and conciseness of the description, regarding the specific operation processes of the system, device and unit described above, reference may be made to the corresponding processes of the methods in the embodiments above, which will not be described again here.

In the embodiments of the present disclosure, it should be understood that the disclosed systems, devices and methods may be implemented in other ways. For example, the devices in the embodiments described above are only schematic. For example, the division of the units is only a division of logical functions. In actual implementation, there may be other divisions. For example, multiple units or components may be combined, or may be integrated into another system. Some features may be omitted, or not implemented. In addition, the displayed or discussed coupling or direct coupling or communication connection may be achieved through certain interfaces, and the indirect coupling or communication connection between the devices or units may be in electrical, mechanical or other forms.

The units described as separate components may or may not be physically separated, and the components displayed as units may or may not be physical units. They may be located in one place, or may be distributed on multiple network units. A part or all of the units may be selected according to actual needs to achieve the purpose of the solutions in the embodiments.

In addition, the functional units in the embodiments of the present disclosure may be integrated into one processing unit. Alternatively, the unit may be physically separated. Alternatively, two or more units may be integrated into one unit. The integrated unit may be implemented in the form of hardware or software functional unit.

When the integrated unit is implemented in the form of a software functional unit and sold or used as an independent product, it may be stored in a computer-readable storage medium. Based on this understanding, the essential part or the part contributed to the prior arts of the technical solutions of the present disclosure, or all or part of the technical solutions, may be embodied as a software product. The software product may be stored in a storage medium, and may include multiple instructions which may enable a computer device (which may be a personal computer, a server, or a network device, etc.) to perform all or part of the steps of the methods in the embodiments of the present disclosure. The storage medium may include a U disk, a mobile hard disk, a read-only memory (ROM), a random access memory (RAM), a magnetic disk, an optical disk or other medium that can store program codes.

The embodiments above are only used to illustrate the technical solutions of the present disclosure, but not intended to limit them. Although the present disclosure has been described in detail with reference to the embodiments above, a person ordinarily skilled in the art should understand that modifications may be made to the technical solutions described in the embodiments or equivalent replacement may be made to some of the technical features. These modifications or replacements will not make essence of the technical solutions to depart from the spirit and scope of the present disclosure.

The invention claimed is:

1. A contrast enhanced imaging method, comprising:
receiving, via a processor, a first instruction input by a user;
determining a first imaging mode from preset imaging modes in response to the first instruction, wherein the first imaging mode comprises a first frame rate, and the first frame rate is pre-configured with first imaging parameters comprising a first imaging range and a first pulse repetition frequency;
transmitting first ultrasound waves in the first pulse repetition frequency to a target object and receiving first ultrasound echoes returned from the target object according to the first imaging mode to obtain first ultrasound echo signals;
generating a first contrast enhanced image having the first frame rate in the first imaging range according to the first ultrasound echo signals;
receiving, via the processor, a second instruction input by the user;
determining a second imaging mode from the preset imaging modes in response to the second instruction, wherein the second imaging mode comprises a second frame rate greater than the first frame rate, and the second frame rate is pre-configured with second imaging parameters comprising a second imaging range less than the first imaging range and a second pulse repetition frequency greater than the first pulse repetition frequency;
transmitting second ultrasound waves in the second pulse repetition frequency to the target object and receiving second ultrasound echoes returned from the target object according to the second imaging mode to obtain second ultrasound echo signals; and
generating a second contrast enhanced image having the second frame rate in the second imaging range according to the second ultrasound echo signals.

2. The method of claim 1, wherein the first frame rate is a pre-configured with fixed frame rate, wherein the pre-configured fixed frame rate of the first imaging mode is smaller than the second frame rate of the second imaging mode.

3. The method of claim 2, wherein
the first imaging parameters further comprise at least one of a first number of times for transmitting ultrasound waves and a first line density; and
the second imaging parameters further comprise at least one of a second number of times for transmitting ultrasound waves and a second line density; and
wherein, the first number of times for transmitting ultrasound waves is greater than the second number of times for transmitting ultrasound waves, or the first line density is greater than the second line density.

4. The method of claim 2, wherein, the second imaging mode is pre-configured with at least two frame rates and each of the at least two frame rates is pre-configured with a corresponding imaging parameter, and the second frame rate is determined from the at least two frame rates.

5. The method of claim 2, wherein, the second imaging mode is pre-configured with at least two frame rates and an execution sequence of the at least two frame rates, wherein each frame rate is pre-configured with a corresponding imaging parameter and an imaging duration, and the method further comprises:
receiving a third instruction; and
wherein, transmitting the second ultrasound waves in the second pulse repetition frequency to the target object and receiving the second ultrasound echoes returned from the target object according to the second imaging mode to obtain the second ultrasound echo signals comprises:
sequentially transmitting the second ultrasound waves to the target object and receiving the second ultrasound echoes returned from the target object according to the execution sequence, the pre-configured imaging parameter and the imaging duration of a corresponding frame rate, in response to the third instruction to obtain the second ultrasound echo signals; and
generating the second contrast enhanced image according to the second ultrasound echo signals comprises:
sequentially generating contrast enhanced images according to the obtained second ultrasound echo signals.

6. The method of claim 1, further comprising:
receiving a fourth instruction; and
stopping transmitting ultrasound waves to the target object and receiving ultrasound echoes returned from the target object in response to the fourth instruction.

7. A contrast enhanced imaging method, comprising:
transmitting, via a probe, first ultrasound waves in a first pulse repetition frequency to a target object and receiving first ultrasound echoes returned from the target object according to a first imaging mode to obtain first ultrasound echo signals, wherein the first imaging mode comprises a first frame rate, and the first frame rate is pre-configured with first imaging parameters comprising a first imaging range and the first pulse repetition frequency;
generating, via a processor, a first contrast enhanced image having the first frame rate in the first imaging range according to the first ultrasound echo signals;
receiving, via the processor, a mode switching instruction to switch to a second imaging mode, wherein the second imaging mode comprises a second frame rate greater than the first frame rate, and the second frame rate is pre-configured with second imaging parameters comprising a second imaging range less than the first imaging range and a second pulse repetition frequency greater than the first pulse repetition frequency;
transmitting, via the probe, second ultrasound waves in the second pulse repetition frequency to the target object and receiving second ultrasound echoes returned from the target object according to the second imaging mode to obtain second ultrasound echo signals; and
generating, via the processor, a second contrast enhanced image having the second frame rate in the second imaging range according to the second ultrasound echo signals.

8. An ultrasound imaging device, comprising:
a probe;

a transmitting circuit which excites the probe to transmit ultrasound waves to a target object;

a receiving circuit which receives ultrasound echoes returned from the target object through the probe to obtain an ultrasound echo signal;

a processor configured to process the ultrasound echo signal to obtain an ultrasound image of the target object;

a display which displays the ultrasound image;

wherein the processor is further configured to:

receive a first instruction input by a user;

determine a first imaging mode from preset imaging modes in response to the first instruction, wherein the first imaging mode comprises a first frame rate, and the first frame rate is pre-configured with first imaging parameters comprising a first imaging range and a first pulse repetition frequency;

transmit first ultrasound waves in the first pulse repetition frequency to the target object and receive first ultrasound echoes returned from the target object according to the first imaging mode to obtain first ultrasound echo signals;

generate a first contrast enhanced image having the first frame rate in the first imaging range according to the first ultrasound echo signals;

receive a second instruction input by the user;

determine a second imaging mode from the preset imaging modes in response to the second instruction, wherein the second imaging mode comprises a second frame rate greater than the first frame rate, and the second frame rate is pre-configured with second imaging parameters comprising a second imaging range less than the first imaging range and a second pulse repetition frequency greater than the first pulse repetition frequency;

transmit second ultrasound waves in the second pulse repetition frequency to the target object and receive second ultrasound echoes returned from the target object according to the second imaging mode to obtain second ultrasound echo signals; and generate a second contrast enhanced image having the second frame rate in the second imaging range according to the second ultrasound echo signals.

9. The device of claim 8, wherein the first frame rate is a pre-configured fixed frame rate, wherein the pre-configured fixed frame rate of the first imaging mode is smaller than the second frame rate of the second imaging mode.

10. The device of claim 9, wherein the first imaging parameters further comprise at least one of a first number of times for transmitting ultrasound waves and a first line density; and the second imaging parameters further comprise at least one of a second number of times for transmitting ultrasound waves and a second line density;

wherein, the first number of times for transmitting ultrasound waves is greater than the second number of times for transmitting ultrasound waves, or the first line density is greater than the second line density.

11. The device of claim 9, wherein, the second imaging mode is pre-configured with at least two frame rates and each of the at least two frame rates is pre-configured with a corresponding imaging parameter, and the second frame rate is determined from the at least two frame rates.

12. The device of claim 9, wherein, the second imaging mode is pre-configured with at least two frame rates and an execution sequence of the at least two frame rates, wherein each frame rate is pre-configured with a corresponding imaging parameter and an imaging duration, and the processor is further configured to:

receive a third instruction input by the user;

and wherein the processor is configured to:

sequentially transmit the second ultrasound waves in the second pulse repetition frequency to the target object and receive the second ultrasound echoes returned from the target object according to the execution sequence, the pre-configured imaging parameter and the imaging duration of a corresponding frame rate, in response to the third instruction to obtain the second ultrasound echo signals; and sequentially generate contrast enhanced images according to the obtained second ultrasound echo signals.

13. The device of claim 8, wherein the processor is further configured to:

receive a fourth instruction; and stop transmitting ultrasound waves to the target object and receiving ultrasound echoes returned from the target object in response to the fourth instruction.

\* \* \* \* \*